United States Patent [19]

Arakawa et al.

[11] 4,304,726
[45] Dec. 8, 1981

[54] PROCESS FOR THE PREPARATION OF CHOLESTEROL DERIVATIVES

[75] Inventors: Yoshio Arakawa, Suita; Atuyuki Takanabe, Hirakata; Yahiro Uemura, Hirakata; Satoshi Funakoshi, Katano; Daisuke Satoh, Nishinomiya, all of Japan

[73] Assignee: The Green Cross Corporation, Osaka, Japan

[21] Appl. No.: 156,091

[22] Filed: Jun. 3, 1980

[30] Foreign Application Priority Data

Jun. 20, 1979 [JP] Japan ................... 54-76767

[51] Int. Cl.³ .............................. C07J 9/00
[52] U.S. Cl. ............................... 260/397.2
[58] Field of Search ..................... 260/397.2

[56] References Cited

U.S. PATENT DOCUMENTS

| | | | |
|---|---|---|---|
| 4,157,391 | 6/1979 | Kitame et al. | 424/238 |
| 4,189,400 | 2/1980 | Proksch et al. | 260/397.2 |
| 4,202,891 | 5/1980 | Schroepfer et al. | 260/397.2 |
| 4,225,525 | 9/1980 | Baggiolini et al. | 260/397.2 |

OTHER PUBLICATIONS

"Steroid Reactors" by Djerossi et al. (1963) pp. 114, 115.

*Primary Examiner*—Elbert L. Roberts
*Attorney, Agent, or Firm*—Cushman, Darby & Cushman

[57] ABSTRACT

New organic dibasic acid half esters of 7-ketocholesterol and of 7-hydroxycholesterol represented by the general formula

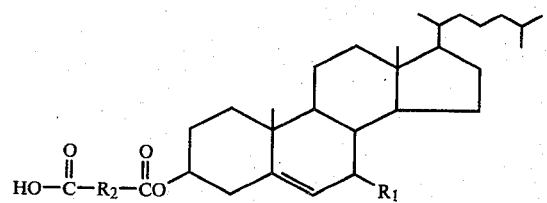

(wherein $R_1$ is =O or —OH and $R_2$ is a $C_1$–$C_5$ alkylene group or a phenylene group) and physiologically acceptable salts thereof. These compounds are effective as an immunosuppressive or an anti-inflammatory agent.

6 Claims, No Drawings

PROCESS FOR THE PREPARATION OF CHOLESTEROL DERIVATIVES

The present invention relates to new cholesterol derivatives and more particularly to new organic dibasic acid half esters of 7-ketocholesterol and of 7-hydroxycholesterol, to physiologically acceptable salts thereof, and to a method for preparing these compounds.

The present inventors found previously that some immunosuppression active substances isolated from the human serum Cohnn's IV-1 paste are identical with 7-ketocholesterol and 7-hydroxycholesterol, and as a result of pharmacological tests on these compounds, further found that they are effective as immunosuppressive agent, particularly as cell-mediated immunosuppressive agent, and also as anti-inflammatory, therapeutic agent [Japanese Patent Application Kokai (Laid-open) No. 104,735/1978].

On account of sparingly water-soluble properties of 7-ketocholesterol and of 7-hydroxycholesterol, which are extremely valuable as a medicine to be investigated on pharmaceutical preparation technique, the present inventors made extensive studies aiming at developments of derivatives thereof improved in water solubility. As a result, they were successful in preparing new compounds, organic dibasic acid half esters of 7-ketocholesterol and of 7-hydroxycholesterol represented by the general formula

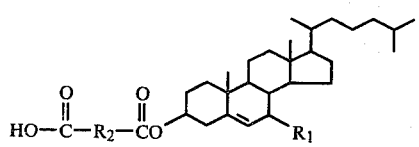

(wherein $R_1$ is =O or —OH and $R_2$ is a $C_1$–$C_5$ alkylene group or a phenylene group) and physiologically acceplable salts thereof.

An object of this invention is to provide new organic dibasic acid half esters of 7-ketocholesterol and of 7-hydroxycholesterol and physiologically acceptable salts thereof as well as a method of preparing them.

Other objects and advantages of this invention will become apparent from the following description.

According to the method of this invention, the organic dibasic acid half esters of 7-ketocholesterol represented by the general formula

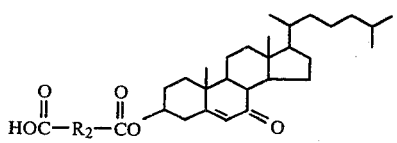

(wherein $R_2$ is the same as mentioned above) can be prepared by partial esterification of 7-ketocholesterol with reactive derivatives of the corresponding organic dibasic acids represented by the general formula

(wherein $R_2$ is the same as defined above), such as succinic acid, adipic acid, glutaric acid, phthalic acid, etc., in the presence of a tertiary amine such as pyridine, triethylamine, dimethylaniline, etc.

Said reactive derivatives of the organic dibasic acids are, for example, acid anhydrides and acid halides, and amounts thereof to be used are usually 1.0 to 3.0 moles per mole of 7-ketochloresterol. The reaction temperature is usually from 60° to 150° C.

The organic dibasic acid half esters of 7-ketocholesterol can also be prepared by oxidizing, by means of a chromic acid group oxidizing agent, the organic dibasic acid half ester of cholesterol obtainable by reacting cholesterol analogue with reactive derivatives of the corresponding dibasic acids represented by formula (IV). Said chromic acid group oxidizing agent is, for example, anhydrous chromic acid, t-butyl chromate, or a dichromate such as potassium dichromate, sodium dichromate. The amount thereof to be used is usually from 3.0 to 15 moles per mole of the organic dibasic acid half ester of cholesterol. The reaction is carried out in a solvent, for example, an organic acid such as acetic acid, propionic acid, or acetic anhydride, or an inert solvent, such as carbon tetrachloride, chloroform, methylene dichloride, benzene or the like, which contains the above organic acid. The reaction temperature is generally 30° to 100° C., though it varies depending upon the oxidizing agent used. For example, in the case where t-butyl chromate is used, it is the boiling point of the solvent used and in the case of anhydrous chromic acid or a salt of dichromic acid, the temperature of 40° to 70° C. is desirable.

Next, the organic dibasic acid half esters of 7-hydroxycholesterol represented by the general formula

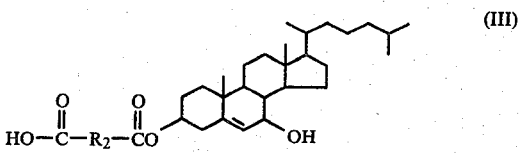

(wherein $R_2$ is the same as mentioned above) can be prepared by subjecting the corresponding organic dibasic acid half esters of 7-ketocholesterol or salts thereof to reduction with a complex metal hydride such as sodium borohydride, potassium borohydride, or lithium aluminum hydride in a solvent such as water, methanol, ethanol, dioxane, tetrahydrofuran, etc. The amount of the metal complex hydride to be used is 1.0 to 10.0 moles per mole of the organic dibasic acid half ester of 7-ketocholesterol. There is no particular restriction on the reaction temperature, but the reaction is usually carried out with cooling at 0° C. or up to room temperature.

The organic dibasic acid half esters of 7-ketocholesterol and of 7-hydroxycholesterol thus obtained can, in compliance with request, be led easily in a usual way to physiologically acceptable salts thereof, for example, alkali salts, such as potassium and sodium salts, alkali earth salts such as calcium salt, ammonium salt, and salts of organic base such as triethylamine, triethanolamine, etc. There are all new compounds unpublished in the past literature, which exhibit prominent effects in immunosuppression, especially in cell-mediated immunosuppression, and anti-inflammation, and in addition, they are soluble in water, so that they are very useful as a medicine.

Experimental data on the usefulness of the compounds of this invention are given below.

(1) Immunosuppressive Action (Experiments in vitro)

In accordance with the PHA method by Cooparband et al. [The Journal of Immunology, 109, (1), 154 (1972)], the compounds of this invention were tested for the 50% inhibitory concentration in the PHA reaction. The results obtained are shown in Table 1. Also, the effect of IRA (Immunoregulatory α-globulin) obtained according to the method of Occhino et al. [The Journal of Immunology, 110, (3), 685 (1973)] was shown as comparative test data. Among these compounds, those of the ester form were used in emulsion employing a copolymer of polyoxyethylene-polyoxypropylene having molecular weight of 8350 as a surfactant, and those of the salt form were used as aqueous solutions.

TABLE 1

Immunosuppressive effect

| Test sample | Concentration for 50% inhibition (μg/ml) |
|---|---|
| 7-ketocholesteryl hydrogen succinate | 4 |
| 7-ketocholesteryl hydrogen phthalate | 4 |
| Sodium 7-ketocholesteryl succinate | 4 |
| Ammonium 7-ketocholesteryl succinate | 4 |
| 7-hydroxycholesteryl hydrogen succinate | 3 |
| Sodium 7-hydroxycholesteryl succinate | 3 |
| 7β-hydroxycholesteryl hydrogen phthalate | 3 |
| Sodium 7β-hydroxycholesteryl phthalate | 4 |
| IRA (comparative sample) | 20 |

(2) Immunosuppressive Action (Experiment in vivo)

Animal experiments were carried out on the compounds of this invention.

Using 25 mice, which were divided to 5 groups each consisting of 5 mice, the samples including a control were administered thereto by intravenous injection for 20 days in succession as follows to examine the effect of each sample on a skin transplantation test:

Group 1, 7-hydroxycholesteryl hydrogen succinate (8 mg/kg/day);

Group 2, 7-ketocholestryl hydrogen succinate (10 mg/kg/day);

Group 3, sodium 7-hydroxycholesteryl succinate (8 mg/kg/day);

Group 4, sodium 7-ketocholesteryl succinate (10 mg/kg/day);

Group 5, a physiological sodium chloride aqueous solution as control.

The ester samples were applied in the form of emulsion employing the surfactant mentioned before, and the salt samples were applied as they are directly dissolved in water. Every sample was made physiologically isotonic with a final concentration of 3% by weight. Each sample was administered once 24 hours before the start of the transplantation tests and thereafter once a day for 20 days.

According to surface observation after 20 days, the groups subjected to administration of the compounds of this invention showed graft survival ratio of about 80 to 90% in contrast to 0% in the case of the control. These results indicate the pharmacological effectiveness of the present compounds as an immunosuppressive agent.

(3) Anti-inflammatory action

Using rats, each of derivatives of 7-hydroxycholesterol and of 7-ketocholesterol shown in Table 2 was administered intraperitoneally to 5 rats of each group in a dose of 50 mg/kg (physiologically isotonic aqueous solution with a concentration of 2.0% by weight), and one hour after the administration, each 0.05 ml of 1% aqueous carrageenin solution as an inflammation-causing substance was subcutaneously inoculated at the hind footpad.

After 4 hours from the inoculation of carrageenin, the size of edema caused on the footpad was measured by means of a volume differential meter to compare with that of the control group which was given to the physiological sodium chloride aqueous solution.

The results are shown in Table 2. The ester samples administered were in the form of emulsion employing a phospholipid as a surfactant, and the salt samples were in the form of physiologically isotonic solution.

TABLE 2

Anti-inflammatory Effect

| Test sample | Swelling rate of edema (%) |
|---|---|
| Control | 82 |
| 7-ketocholesteryl hydrogen succinate | 30 |
| 7-ketocholesteryl hydrogen phthalate | 28 |
| Sodium 7-ketocholesteryl succinate | 30 |
| Ammonium 7-ketocholesteryl succinate | 30 |
| 7-hydroxycholesteryl hydrogen succinate | 29 |
| Sodium 7-hydroxycholesteryl succinate | 28 |
| 7β-hydroxycholesteryl hydrogen phthalate | 30 |
| Sodium 7β-hydroxycholesteryl phthalate | 31 |

(4) Amount and method of administration

The compounds of general formula (I) in this invention, which were examined by animal experiments on 50% effective dose in immunosuppressive activity and in anti-inflammatory activity are, in therapeutic application, preferred to be in the form of injectable preparation, and the desirable dose thereof in injection is 10 to 1000 mg of total amount/kg. These compounds are also effective in external and oral administrations, but the doses in these cases are 40 to 2000 mg of total amount/kg. When they are applied externally, the total dose may be small because they can act topically.

When used for injection, the compounds of this invention are used preferably as a 0.1 to 1% aqueous solution, and in case of ester type, the compounds are used in the form of physiologically isotonic aqueous dispersion emulsified by use of a suitable surfactant.

When administered in the form of an aqueous solution, the addition of a known stabilizer for steroids (e.g., albumin) is much advantageous. It is sufficient to add in an amount of 0.1 to 5% by weight in the aqueous solution.

Moreover, addition of propylene glycol, polyethylene glycol, or glycerin as a solubilizing aid is favorable. It suffices to add in an amount of 0.1 to 8.0% by weight in the aqueous solution.

In oral administration, the compounds of this invention can be made into tablets or liquid preparations suitable for oral administration in the manner familiar to persons skilled in the art.

In external administration, they can be applied by making them into ointment in the manner familiar to persons skilled in the art. This administration manner is effective since the preparation acts directly on the affected portion.

(5) Acute Toxicity Test

Acute toxicity tests were performed using rats, each group consisting of 5 rats each weighing approximately 200 g, on 7-ketocholesteryl hydrogen succinate, 7-ketocholesteryl hydrogen phthalate, sodium 7-ketocholesteryl succinate, ammonium 7-ketocholesteryl succinate, 7-hydroxycholesteryl hydrogen succinate, 7β-hydroxycholesteryl hydrogen phthalate, sodium 7-hydroxycholesteryl succinate, and sodium 7β-hydroxycholesteryl phthalate. Each of the compounds of salt type was made into a physiologically isotonic aqueous solution, and each of the compounds of ester type was dispersed with a surfactant and by ultrasonic wave treatment to give a uniform dispersion. Thereafter, each of them was administered intraperitoneally in an amount of 250 mg/kg, 500 mg/kg, 750 mg/kg, or 1000 mg/kg. After 5-days' observation, no rat died.

As described above, the compounds of this invention have practically no toxicity and also no antigenic property so that they can be offered as an excellent immunosuppressive or anti-inflammatory agent.

The method for preparing compounds of this invention is illustrated by way of the following examples.

EXAMPLE 1

In 50 ml of pyridine was dissolved 5 g of 7-ketocholesterol, and 1.8 g of succinic anhydride was added thereto. The mixture was heated at 90° C. for 8 hours, allowed to stand over night at room temperature. The reaction mixture was poured into 500 ml ice-cold water, and acidified with hydrochloric acid, and isolated crystals were filtered off, dissolved in ethanol, decolorized by addition of active carbon, and then filtered. Water was added to the filtrate, and the isolated crystals were filtered off. The crystals were recrystalized from aqueous ethanol to obtain 5.4 g of scalelike crystalline 7-ketocholesteryl hydrogen succinate, m.p. 187.5°–189.5° C.

Elementary analysis: $C_{31}H_{48}O_5$: Theoretical value (%): C, 74.36; H, 9.66. Experimental value (%): C, 74.54; H, 9.59.

Infrared absorption maxima (KBr tablet): 1735, 1705, 1670, 1170 $cm^{-1}$

EXAMPLE 2

In 50 ml of pyridine was dissolved 5 g of 7-ketocholesterol, and 2.7 g of phthalic anhydride was added thereto. The mixture was treated in the same manner as in Example 1 to obtain 5.8 g of 7-ketocholesteryl hydrogen phthalate, m.p. 168.5°–171.0° C.

Elementary analysis: $C_{35}H_{48}O_5$: Theoretical value (%); C, 76.61; H, 8.82. Experimental value (%): C, 76.80; H, 8.79.

Infrared absorption maxima (KBr tablet): 1735, 1705, 1670, 1170 $cm^{-1}$

EXAMPLE 3

In 22 ml of methanol was suspended 733 mg of 7-ketocholesteryl hydrogen succinate, and 3.38 ml of methanol solution containing 1% sodium methylate was added thereto with stirring at room temperature. Stirring was continued for 20 minutes at room temperature. After completion of the reaction methanol was distilled off under reduced pressure to obtain 718 mg of sodium 7-ketocholesteryl succinate in the form of white powder.

EXAMPLE 4

In 5 ml of methanol was suspended 100 mg of 7-ketocholesteryl hydrogen succinate, and 1.6 ml of methanol solution containing 0.5% sodium hydroxide was added thereto with stirring. Thereafter, the mixture was treated in the same manner as in Example 3 to obtain 100 mg of sodium 7-ketocholesteryl succinate in the form of white powder.

EXAMPLE 5

In 5 ml of methanol was suspended 100 mg of 7-ketocholesteryl hydrogen succinate, and dry ammonia gas was introduced thereinto up to saturation with stirring. Thereafter, the mixture was treated by the same manner as in Example 3 to obtain 98 mg of ammonium 7-ketocholesteryl succinate in the form of white powder.

EXAMPLE 6

In 10 ml of carbon tetrachloride was dissolved 2.0 g of cholesteryl hydrogen succinate while stirring the solution vigorously at 80° C., the mixture of t-butyl chromate (9 times by mole) 20 ml of carbon tetrachloride, 6 ml of acetic acid, and 3 ml of acetic anhydride was added dropwise gradually. After 10-hours' vigorous stirring at 80° C., the reaction mixture was allowed to stand over night at room temperature. Thereafter, while stirring with ice-cooling, the reaction mixture was admixed with 45 ml of 10% aqueous oxalic acid solution gradually and further with 1.5 g of oxalic acid, and stirring was continued with ice-cooling for 2 hours and subsequently at room temperature for 2 hours. Thereafter the carbon tetrachloride layer was separated off, combined with the extract solution obtained by extracting the water layer 3 times with each 10 ml of carbon tetrachloride, washed with water, dehydrated with anhydrous sodium sulfate, and then subjected to distillation to remove carbon tetrachloride. The resulting residue was recrystallized from an aqueous ethanol to obtain 830 mg of 7-ketocholesteryl hydrogen succinate. The infrared absorption spectrum of this product corresponded to that of the compound obtained in Example 1.

EXAMPLE 7

While stirring 2.5 g of cholesteryl hydrogen succinate together with 60 ml of acetic acid at 54° to 60° C., each 125 mg of anhydrous chromic acid was added thereto 12 times at 10-minutes' intervals. After vigorous stirring at 54° to 60° C. for further 2.5 hours, the reaction mixture was cooled back to room temperature, admixed with 0.5 ml of 95% ethanol with stirring, and then gradually with 20 ml of water, and allowed to stand over night at 5° to 10° C. The crystalline product isolated was filtered off, washed with a cold 50% aqueous acetic acid, and then dried. The resulting product was recrystallized from an aqueous ethanol to obtain 800 mg of 7-ketocholesteryl hydrogen succinate. The infrared absorption spectrum of this product corresponded to that of the product obtained in Example 1.

EXAMPLE 8

In 100 ml of methanol was dissolved 3.75 g of sodium 7-ketocholesteryl succinate. While stirring and ice-cooling, 820 mg of sodium borohydride was gradually added thereto, and stirring was continued with ice-cooling for 10–15 minutes and further at room temperature for one hour. After excess of sodium borohydride had been decomposed by adding 2 ml of acetic acid, the reaction mixture was diluted with 150 ml of water, acidified with hydrochloric acid, and the crystals isolated were recovered by filtration. The resulting crystals were recrystallized from cyclohexane to obtain 3.43 g of needle-shaped crystalline 7-hydroxychloresteryl hydrogen succinate, m.p. 150°–154° C. This product was a mixture of 7α-hydroxy isomer and 7β-hydroxy isomer in the proportion of 1: about 3. 7β-hydroxy isomer was major.

Elementary analysis: $C_{31}H_{50}O_5$: Theoretical value (%): C, 74.06; H, 10.02. Experimental value (%): C, 74.21; H, 9.96.

Infrared absorption maxima (KBr tablet): 3500, 1730, 1705, 1165 cm$^{-1}$

EXAMPLE 9

By treating 1.0 g of 7-hydroxycholesteryl hydrogen succinate in the same manner as in Example 3, 983 mg of the sodium salt thereof was obtained in the form of white powder.

EXAMPLE 10

By treating 1.6 g of sodium 7-ketocholesteryl phthalate in the same manner as in Example 8, 1.3 g of 7-hydroxycholesteryl hydrogen phthalate was obtained. The product was subjected to fractional recrystallization from n-propanol to obtain 129 mg of 7α-hydroxy isomer and 792 mg of 7β-hydroxy isomer.

7α-hydroxy isomer:
m.p.: 176°–177° C. (decomposed)

Elementary analysis: $C_{36}H_{50}O_5$: Theoretical value (%): C, 76.33; H, 9.15. Experimental value (%): C, 76.15; H, 9.21.

Infrared absorption maxima (KBr tablet): 3370, 1715, 1700, 1300 cm$^{-1}$

7β-hydroxy isomer:
m.p.: 149°–153° C. (decomposed)

Elementary analysis: $C_{35}H_{50}O_5$: Theoretical value (%): C, 76.33; H, 9.15. Experimental value (%): C, 76.61; H, 9.02.

Infrared absorption maxima (KBr tablet): 3320, 1720, 1680, 1285 cm$^{-1}$

EXAMPLE 11

By treating 400 mg of 7β-hydroxycholesteryl hydrogen phthalate in the same manner as in Example 3, 395 mg of the sodium salt thereof was obtained in the form of white powder.

What is claimed is:

1. A method for preparing an organic dibasic acid half ester of 7-hydroxycholesterol, which comprises reducing the corresponding organic dibasic acid half ester of 7-ketocholesterol or a salt thereof in a solvent with a complex metal hydride.

2. A method according to claim 1, wherein the organic dibasic acid is succinic acid, adipic acid, glutaric acid, or phthalic acid.

3. A method according to claim 1, wherein said complex metal hydride is used in an amount of from 1.0 to 10.0 moles per mole of the organic dibasic acid half ester of 7-ketocholesterol.

4. A method according to claim 3, wherein said complex metal hydride is sodium borohydride, potassium borohydride, or lithium aluminum hydride.

5. A method according to claim 1, wherein said solvent is water, methanol, ethanol, dioxane, or tetrahydrofuran.

6. A method according to claim 1, wherein the reaction temperature is from 0° C. to room temperature.

* * * * *